United States Patent [19]
Knifton et al.

[11] Patent Number: 6,147,261
[45] Date of Patent: Nov. 14, 2000

[54] DIAMINOALKANE SYNTHESES VIA SELECTIVE AMINATION OF HYDROXYALDEHYDES

[75] Inventors: John Frederik Knifton; Daniel John Janitor, both of Houston, Tex.

[73] Assignee: Shell Oil Corporation, Houston, Tex.

[21] Appl. No.: 09/442,234

[22] Filed: Nov. 17, 1999

Related U.S. Application Data

[60] Provisional application No. 60/109,572, Nov. 23, 1998.

[51] Int. Cl.$^7$ .......................... C07C 209/16; C07C 209/26
[52] U.S. Cl. ............................................ 564/473; 564/471
[58] Field of Search ...................... 564/471, 473

[56] References Cited

U.S. PATENT DOCUMENTS

| | | | |
|---|---|---|---|
| 3,270,059 | 8/1966 | Winderl et al. | 260/583 |
| 3,520,933 | 7/1970 | Adam et al. | 260/585 |
| 4,152,353 | 5/1979 | Habermann | 260/585 B |
| 4,153,581 | 5/1979 | Habermann | 252/472 |
| 4,158,017 | 6/1979 | Merger et al. | 564/473 |
| 4,197,260 | 4/1980 | Siclari et al. | 260/585 C |
| 4,409,399 | 10/1983 | Swift et al. | 564/473 |
| 4,683,336 | 7/1987 | Blackhurst | 564/480 |
| 4,772,750 | 9/1988 | Habermann | 564/472 |
| 4,806,690 | 2/1989 | Bowman | 564/480 |
| 5,055,618 | 10/1991 | Kampmann et al. | 564/473 |
| 5,475,141 | 12/1995 | Kos et al. | 564/473 |

FOREIGN PATENT DOCUMENTS

| | | | |
|---|---|---|---|
| C 824 492 | 12/1951 | Germany. | |
| 798 094 | 1/1981 | Russian Federation | B01J 21/04 |

OTHER PUBLICATIONS

Josef Pašek et al, "Equilibrium Conditions for Amination of Alcohols and Carbonyl Compounds," *Ind. Eng. Chem. Prod. Res. Develop.*, 11, 3, 333–337 (1972).

Alfons Baiker et al., "Catalytic Amination of Long Chain Aliphatic Alcohols," *Ind. Eng. Chem., Prod. Res. Dev.*, 16, 3, 261–266 (1977).

Michael E. Ford et al, Selective Catalytic Synthesis of Mixed Alkylamines and Polyfunctional Amines, *Catalysis of Organic Reactions*, D. W. Blackburn, ed., Ch. 14, pp. 219–240 (1990).

Charles M. Barnes et al., "Ethylenediamine by Low–Pressure Ammonolysis of Monoethanolamine," *Ind. Eng. Chem. Prod. Res. Dev.*, 20, 2, 399–407 (1981).

Michael E. Ford et al., "Shape–Selective Mordenite–Catalyzed Amination of Ethanolamine to Ethylenediamine," *Journal of Molecular Catalysis*, 60, 11–17 (1990).

K. Segawa et al., "Selective Synthesis of Ethylenediamine from Ethanolamine over Modified H–Mordenite Catalyst," J. W. Hightower, et al., Eds., *11$^{th}$ International Congress on Catalysis—40$^{th}$ Anniversary*, Studies in Surface Science and Catalysis, 101, ©1996 Elsevier Science B.V.

H. Kimura et al., "Cu/Ni Colloidal Dispersions Stabilised by Calcium and Barium Stearates for the Amination of Oxo–Alcohols," *Catalysis Letters 40*, ©J. C. Blatzer AG, Science Publishers, 123–130 (1966).

J. F. Knifton and D. J. Janitor, "Diaminoalkane Syntheses Via Selective Amination of Dihydric Alcohols," U.S. Patent Application Serial No. 60/109,559, filed Nov. 23, 1998 (Docket No. TH–1321).

*Primary Examiner*—Johann Richter
*Assistant Examiner*—Brian J. Davis
*Attorney, Agent, or Firm*—Del S. Christensen

[57] ABSTRACT

Disclosed is a process for producing diaminoalkanes which comprises reacting a hydroxyalkanal characterized by two to six carbons, preferably 3-hydroxypropanal, with excess ammonia and sufficient hydrogen to stabilize a nickel or cobalt-containing hydroamination catalyst, at a temperature of at least 50° C. and a pressure of at least 500 psig, until there is substantial formation of the desired diaminoalkane, wherein said catalyst comprises at least one metal selected from the group consisting of nickel and cobalt, or mixtures thereof, optionally in the presence of one or more promoters.

27 Claims, No Drawings

DIAMINOALKANE SYNTHESES VIA SELECTIVE AMINATION OF HYDROXYALDEHYDES

CROSS-REFERENCE

This application claims the benefit of U.S. Provisional Application No. 60/109,572, filed Nov. 23, 1998, the entire disclosure of which is hereby incorporated by reference This application is related to U.S. patent application Ser. No. 60/109,559, filed of even date and incorporated by reference herein in its entirety.

FIELD OF THE INVENTION

This invention relates to hydroamination. In particular this invention is related to a process for the selective hydroamination of a hydrocarbon having dual functionalities to yield a diaminoalkane. In the preferred embodiment this invention provides a process for the selective hydroamination of 3-hydroxypropanal (HPA) to yield 1,3-diaminopropane and its homologues in one step. The process can also be accomplished in two steps with 3-amino-1-propanol as the key intermediate.

BACKGROUND

The hydroamination of commodity and specialty alcohols, aldehydes and ketones to manufacture the corresponding aliphatic amines is known in the art. The selection of a catalyst with optimal advantages has also been the focus of much research. Aliphatic amines are of considerable industrial importance and find applications in many facets of modern technology, agriculture and medicine.

For example, U.S. Pat. No. 3,270,059 discloses the production of diaminoalkanes by passing an alkanediol, alkanolamine, alkylene oxide, or alkyleneimine along with either ammonia or an alkylamine in the presence of hydrogen and at an elevated temperature over a catalyst which contains sintered cobalt or nickel.

In an article titled "Equilibrium Conditions for Amination of Alcohols and Carbonyl Compounds", i Ind. Eng. Chem. Prod Res. Develop., 11, 3, 333–337(1972), Josef Pasek, et al. described the influence of pressure, temperature, and initial composition, on the equilibrium content of primary, secondary, and tertiary amines in unsaturated compounds.

Alfons Baiker et al., in an article titled "Catalytic Amination of Long Chain Aliphatic Alcohols", *Ind. Eng. Chem., Prod. Res. Dev.*, 16, 3, 261–266 (1977), discuss the amination of dodecanol with dimethylamine and note a preference for using a copper catalyst.

In Russian Patent No. 798094 (1981) there is disclosed the preparation of primary aliphatic amine compounds by reduction-amination of 4–19 carbon aldehydes using liquid ammonium and hydrogen.

The amination of alcohols, aldehydes, and ketones using catalysts containing nickel, copper, or both, has been also been described, for example, in U.S. Pat. No. 4,153,581 and U.S. Pat. No. 4,152,353 and U.S. Pat. No. 4,409,399. These patents do not appear to contemplate the production of diamines.

French patent FR 2 656 864 describes a two-stage process for preparing aliphatic diamines from the corresponding dialdehydes.

DE-C 824 492 discloses a process for preparing aliphatic diamines having a long chain by introducing the corresponding dialdehyde.

The process disclosed in U.S. Pat. No. 4,683,336 employs a catalyst comprising carbonates of copper, nickel, and cobalt, or mixtures thereof to produce amines from aliphatic alcohols or aliphatic aldehydes.

U.S. Pat. No. 4,806,690 discloses a method of preparing amines from an alcohol, aldehyde, ketone or mixture thereof, in the presence of a catalyst containing about 1 to 20% cobalt, 75 to 95% copper, 1 to 16% of a third component selected from iron, zinc, zirconium, and mixtures thereof. The preferred embodiment demonstrates the reductive amination of MEA.

In an article titled "Ethylenediamine by Low-Pressure Ammonolysis of Monoethanolamine", *Ind. Eng. Chem. Prod. Res. Dev.,* 20, 2, 339–407 (1981), by Charles Barnes et al., there is a detailed study of a catalytic route to ethylenediamine and monoethanolamine.

In an article titled "Shape Selective Mordenite-Catalyzed Amination of Ethanolamine to Ethylenediamine", *Journal of Molecular Catalysis,* 60, 11–17 (1990), M. E. Ford et al. disclose the use of hydrogen mordenite and dealuminated hydrogen mordenite to catalyze the reaction of ethanolamine with ammonia to form ethylenediamine at low pressure.

In *Catalysis of Organic Reactions,* Blackburn, D. W., ed., 1990, at Chapter 14, M. Ford et al. review the selective synthesis of mixed alkyl amines by amine-alcohol reactions over hydrogen phosphate.

U.S. Pat. No. 5,055,618 teaches the preparation of an $\alpha,\omega$-diamine from an $\alpha\omega$-dialdehyde by a method which allows the reaction to be carried out even at relatively high temperatures. This process makes use of the presence of water in the reaction of the dialdehyde and primary amine.

U.S. Pat. No. 5,475,141 discloses that both monoaldehydes and organic compounds having more than one aldehyde group can be reductively aminated in a single stage, by combining an aldehyde and a diluent, where in the case of an alcohol or water as diluent, the mixture is combined at sufficiently low temperatures for no hemi-or semiacetal or no aldehyde hydrate to be formed in the mixture, and by bringing the mixture practically simultaneously into contact with ammonia, a hydrogenation catalyst and hydrogen.

In an article titled "Selective Synthesis of Ethylenediamine from Ethanolamine Over Modified H-Mordenite Catalyst", $11^{th}$ International Congress on Catalysis—$40^{th}$ Anniversary, *Studies in Surface Science and Catalysis,* 101, 267, (1996) J. W. Hightower et al. (Eds.) Elsevier Science, K. Segawa et al. disclose that a zeolitic catalyst mordenite, treated with ethylenediamine, displayed high activity and selectivity for the formation of ethyleneamine, with small amounts of ethyleneimine and piperizine side products.

In the foregoing references there does not appear to be a disclosure of the amination of a compound such as a hydroxyaldehyde, to an aliphatic diamine. It would be very desirable in the art if a process were available for aminating a compound containing hydroxy and aldehyde functions which is available in large volumes, such as, for example 3-hydroxypropanal, to form 1,3-diaminopropane. This would provide an attractive route to an added-value commodity chemical. These diamines could find large volume applications in polyamide resins as monomer/comonomers, as well as price-competitive usage in lube oils, epoxies, hot melt adhesives, and surfactants. They might also be useful in fuel additives, chelating agents, fungicides, and plastic lubricants. It would also be very desirable if such a reaction could take place in one step with high selectivity.

SUMMARY

In accordance with the foregoing, there is disclosed a hydroamination process which comprises reacting a hydroxyalkanal characterized by two to six carbons, preferably 3-hydroxypropanal, with excess ammonia and sufficient hydrogen to stabilize a catalyst which comprises at least one metal selected from the group consisting of nickel and cobalt, or mixtures thereof, optionally supported or as a bulk-metal catalyst, and optionally in the presence of one or more promoters, at a temperature of at least 50° C. and a pressure of at least 500 psig until there is substantial formation of the desired diaminoalkane. Said hydroamination exhibits good selectivity for the desired diaminoalkanes and may be conducted batchwise or in a continuous reactor system.

DETAILED DESCRIPTION OF THE INVENTION

In the broader aspect of this invention diaminoalkanes are prepared from a hydroxyalkanal preferably in a solvent, in the presence of excess ammonia and sufficient hydrogen to stabilize the catalyst, at a temperature of at least 50° C. and at a pressure of at least 500 psig, and separated, optionally, by fractional distillation. The reaction can take place in one or two steps.

The amination reaction of this invention to prepare diaminoalkanes from hydroxyalkanals in the presence of ammonia and hydrogen in one step can be represented by the following general equation (Equation I):

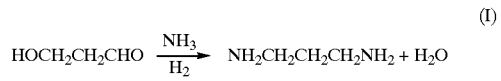

(I)

The production of 1,3-diaminopropane through two-step selective amination of 3-hydroxypropionaldehyde involving the intermediate generation of 3-amino-1-propanol may be described by the following equations (Equation II and III):

(Step 1)

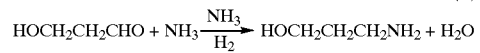

(II)

(Step 2)

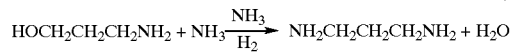

(III)

In step (1), using, for example, a supported nickel catalyst, the intermediate 3-amino-1-propanol is obtained in ca. 80% yield at 120° C. In step (2), Equation III, using a Raney cobalt catalyst with molybdenum and nickel promoters, 1,3-diaminopropane is generated in ca. 50% yields at quantitative 3-amino-1-propanol conversional levels.

The selective amination of 3-hydroxypropionaldehyde yields 1,3-diaminopropane (1,3-DAP) and its homologues. The specific homologues include dipropylene triamine (DPTA) and tripropylene tetramine (TPTA). All three classes of amine were identified through a combination of gc and gc-ms/ir techniques.

The feedstock used in the practice of this invention comprises a hydrocarbon having from two to six carbons and characterized by dual functionalities, preferably separated by only one or more carbons. This would include hydroxyalkanals having two to four carbons, and mixtures of same. Examples could include 3-hydroxypropanal, 4-hydroxybutanal, and 3-hydroxybutanal.

The process is particularly suited to the amination of 3-hydroxypropanal. 3-hydroxypropanal has unique properties compared with other aldehydes. This compound is extremely reactive. It undergoes oligomerization and polymerization quite readily. It must be kept cold and should not be too concentrated. Therefore the 3-hydroxypropanal is preferably fed into the reactor in a suitable solvent.

Solvents may include water, and functionalized hydrocarbons having up to about twenty carbons per molecule, as well as mixtures thereof. Suitable solvents would include aliphatic ethers and tertiary alkanols having up to six carbons. They may include, for example, methyl tertiary-butyl ether and tertiary-butanol. Generally, primary and secondary alcohols would not be suitable. The preferred embodiment discloses the use of an aqueous solution of 3-hydroxypropanal. The amount of 3-hyroxypropanal in the aqueous solution may be from about one to about 50%, but the preferred range is from about 20 to 30% and the use of a 25% aqueous solution is demonstrated in the examples. In the preferred embodiment, a solution of about 25% aqueous 3-hydroxypropanal is fed into a continuous flow reactor.

Whether the process is conducted in one or two steps, the reaction takes place in the presence of excess ammonia and sufficient hydrogen to stabilize the catalyst. The nitrogen source is required to be ammonia, preferably in gaseous form. The amination conditions to be utilized suitably include the use of from 5 to 200 moles of ammonia per hydroxyl and aldehyde equivalent of feedstock and from about 0.1 to about 100 mole equivalents of hydrogen per hydroxyl and aldehyde equivalent of feedstock.

A suitable catalyst comprises at least one Group VIII metal, optionally on a support. Promoters may also be used. Suitable metals include cobalt, nickel, copper, and molybdenum. Particularly effective catalyst compositions in accordance with the present invention are Raney cobalt, Raney nickel, supported and bulk-metal nickel or cobalt, as well as mixtures thereof, optionally with a one or more promoters. The preferred catalysts are Raney cobalt and Raney nickel. Raney nickel and Raney cobalt are catalysts manufactured by W. R. Grace & Co. Raney cobalt catalysts are composed of cobalt, nickel and optionally they also contain molybdenum; on an oxide-free basis they may comprise about 10 to 80% cobalt. Raney nickel catalysts are composed of nickel, plus optionally copper, chromium and molybdenum and contain, on an oxide-free basis, from about 10 to 80 wt % nickel. Especially preferred is a Raney cobalt or nickel catalyst containing from about 50 to 60 wt % cobalt or nickel.

In some examples the catalyst was used with one or more promoters. Suitable promoters include smaller amounts of one or more additional Group VIII metals, and metals from Group IB and VIB of the Periodic Table. This includes chromium, molybdenum, tungsten, and copper.

The catalyst may be on a support. Supports may be selected from Groups II, III, IV, or V of the Periodic Table. The preferred supports include magnesia, alumina, silica, zirconia, and titania, as well as mixtures thereof. Where a support is used, it is preferably alumina or silica. Said catalyst may also be bulk-metal catalysts prepared through coprecipitation of the different metal salts, as their carbonates, etc. The nickel or cobalt bulk-metal catalysts may also contain other metals, particularly copper, chromium, and molybdenum. The nickel or cobalt content of such bulk-metal catalysts is typically 10 to 80%. Said catalysts may be employed in many different forms, including tablets, extrudates, powders, etc.

The catalyst is preferably introduced into the reaction zone initially.

The process takes place under conditions which are generally milder than often observed in amination chemistry in the art. The temperature should be at least about 50° C. A suitable range is from about 80° C. to about 250° C. The preferred range is from about 100° C. to about 200° C., and a particularly preferred range for the one-step process is from about 140° C. to about 180° C. One-step hydroamination of 3-hydroxypropanal generally requires temperatures in excess of 140° C., but an upper limit of ca. 200° C. is set by the limited stability of the low molecular weight amines/hyroxyaldehyde mixtures in the presence of transition-metal catalysts—even in the presence of a large excess of ammonia.

A suitable temperature range for the first step of the two-step process (Equation II) is from about 100–150° C., preferably from about 120–140° C. A suitable temperature range for the second step (Equation III) is about 140–200° C., preferably about 160–185° C.

The pressure should be at least about 500 psi. A suitable range is from about 500 psi to about 5000 psi. The preferred range is from about 1000 psi to about 3000 psi, and particularly preferred is from about 2000 to 2500 psi.

When the reaction is conducted on a continuous basis using the described nickel or cobalt catalysts liquid feed rates may range from about 0.1 to 5.0 LHSV. A preferred range is from about 0.4 to 2.0 LHSV.

The reaction mixture formed as a result of the amination of the 3-hydroxypropanal may be recovered and fractionated in any suitable manner, such as by fractional distillation, to obtain unreacted feed components, by-products, and the desired diaminopropane.

The products have been identified in this work by one or more of the following analytical procedures; viz, gas-liquid chromatography (gc), infrared (ir), mass spectrometry (ms), or a combination of these techniques. All temperatures are in degrees centigrade and all pressures in pound per square inch (psi). The process of the invention can be conducted in a batch, semi-continuous, or continuous manner.

In the one-step hydroamination, temperature range 160–180° C., at quantitative 3-hydroxypropanal conversion levels, the typical effluent sample comprises 28 to 37% 1,3-diaminopropane (1,3-DAP, ex. 2, 6, 7, and 8, basis gc analyses, FI detector) with dipropylenetriamine(DPTA) as a major coproduct (10–19% yield). Here the selected catalysts include a Raney cobalt catalyst with nickel/molybdenum promoters (ex. 2 and 8), a Raney nickel catalyst (ex. 6), and a bulk-metal nickel catalyst comprising 50% nickel and 1.8% molybdenum oxide (ex. 7). Conversions of >80 wt % or more and high 1,3-DAP selectivities are obtainable with the process of the present invention, such that only trace quantities of unreacted feedstock and lesser amounts of DPTA, TPTA, PDO, etc. co-products are present in the reaction mixture. A supported nickel catalyst also provides a similar product distribution (ex. 3).

The 1,3-DAP, DPTA, TPTA products were separated by fractional distillation and identified through a combination of gc and gc-ms/ir techniques. Smaller quantities of N-alkylated diamines, such as N,N-dimethyl-1,3-diaminopropane and N-propyl-1,3-diaminopropane, were also confirmed via gc-ms/ir, together with 1,3-PDO and 2(2-hydroxyethyl)-1,3-dioxane, as well as certain heavier polyamines. Interestingly, there appears to be no evidence for the formation of piperazine-type derivatives during this C-3 bridge amination.

By contrast, poor hydroamination of a 25% aqueous solution of 3-hydroxypropanal to 1,3-DAP was realized in ex. 11 using a cobalt-copper catalyst of the prior art (see Table IX).

In the case of the two-step procedure for making 1,3-diaminopropane (Equations II and III), the 3-amino-1-propane (APO) intermediate was first generated in 84% yield under relatively mild hydroamination conditions (120° C., LHSV 0.4) using a supported-nickel catalyst from Engelhard (Ni-1404, T 3/16", 69% nickel, ex. 12). Identification was by gc-ms/ir. Major co-products include 1,3-propanediol (2.5%), 1,3-diaminopropane (1.2–1.6%), plus lights. Hydroxypropanal conversion was essentially quantitative. A subsequent reamination of this 3-amino-1-propanol (APO) intermediate, as an aqueous 25% solution, produced 1,3-diaminopropane in 50% selectivity at 180° C., LHSV 0.4, using the Raney cobalt catalyst, R-2796 (ex. 13). The major co-products of this second stage, higher temperature, amination were DPTA (ca. 29%) and tripropylenetetramine (TPTA, 12%). Again, there was no gc-ms/ir evidence for cyclic (piperazine-type) derivatives and N-propyl-1,3-diaminopropane was the major N-alkylated material. The 1,3-diaminopropane may be isolated from the crude, liquid, polyamine product via atmospheric distillation. Amination of APO over six days generated several hundred grams of crude DAP and its homologues. Ramping the amination temperature slightly (180–185° C.) allowed activity to be maintained and conversion held at about 85%. It may be possible to further limit the extent of DAP homologation, and thereby further raise the DAP selectivity, by lowering the water content of APO feed, raising the LHSV, and providing more ammonia partial pressure.

In the first step of the two-step process yields of 3-amino-1-propane of ca. 84% are achieved; and a selectivity to 1,3-diaminopropane +DPTA of 78% in step (2) is attained.

Most examples have been conducted in a 50 cc capacity, continuous reactor system operated in the liquid-full, plug-flow mode, and fitted with the appropriate controls. The feedstocks were crude, aqueous, 25% 3-hydroxypropanal solutions with hydroamination taking place over a range of temperatures from about 100° C. to about 200° C.

To illustrate the process of the invention, the following examples are given. It is understood, however, that the examples are given only in the way of illustration and are not to be regarded as limiting the invention in any way.

EXAMPLES

A 50 cc continuous upflow reactor was employed in examples 1 to 13. The reactor was charged with the various nickel or cobalt catalysts, which are labeled in each chart. The 3-hydroxypropionaldehyde was introduced in a solvent and excess ammonia and hydrogen were passed over the catalyst bed as it was heated to 100° C. The temperature was then gradually increased.

Examples 1–10

Examples 1–10 and Tables I through VIII summarize data for the one-step process for making 1,3-diaminopropane (1,3-DAP) from 3-hydroxypropanal or 3-amino-1-propanol. In these examples the catalyst identified in each chart was charged to the stainless-steel reactor system in an amount of 50 g. The 3-hydroxypropanal was fed to said reactor upflow, as a 25% aqueous solution, along with excess ammonia and controlled quantities of hydrogen. The ammonia/3-hydroxypropanal feed molar ratio was between 18 and 35. The hydrogen feed rate was 5 liters/hr. The ammonia plus 3-hydroxypropanal solution feed rate was 20–100 cc/hr. Operating pressure was 2300 psi. Effluent products were collected in stainless-steel bombs and analyzed by gc and gc-ms/ir techniques.

TABLE I

HPA AMINATION

| Ex. | CATALYST | TEMP. (°C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 1 | Raney Co., Grace 54% Co + Ni/Mo, R-2786 | 100 | 0.4 | 34 | 48.2 |  |  |  | 10.0 | 12.2 |
|  |  |  |  |  | 49.5 |  |  |  | 11.2 | 13.8 |
|  |  | 120 | 0.4 | 34 | 48.1 |  |  |  | 12.5 | 16.4 |
|  |  |  |  |  | 48.1 |  |  |  | 12.7 | 15.4 |
|  |  | 140 | 0.4 | 23 | 40.0 | 3.0 |  |  | 10.0 | 18.3 |
|  |  |  |  |  | 38.5 | 3.3 |  |  | 10.7 | 16.5 |
|  |  | 160 | 0.4 | 35 | 16.1 | 18.4 | 10.6 |  | 5.3 | 1.8 |
|  |  |  |  |  | 13.8 | 19.6 | 10.2 |  | 4.6 |  |
|  |  | 180 | 0.4 |  | 19.8 | 14.9 | 9.1 | 2.6 |  |  |
|  |  |  |  |  | 20.4 | 15.8 | 10.8 | 3.1 |  |  |
|  |  | 200 | 0.4 | 38[b] |  | 13.9 |  |  |  |  |
|  |  |  |  |  |  | 13.6 |  |  |  |  |
| Ex. 2 | Raney Co., Grace 52% Co + Ni/Mo, R-2796 | 100 | 0.4 | 34 | 46.4 |  |  |  | 9.0 | 16.9 |
|  |  |  |  |  | 48.9 |  |  |  | 10.1 | 19.8 |
|  |  | 120 | 0.4 | 32 | 57.7 |  |  |  | 8.2 | 16.2 |
|  |  |  |  |  | 58.4 |  |  |  | 7.9 | 13.5 |
|  |  | 140 | 0.4 | 27 | 43.9 | 6.4 |  |  | 7.7 | 17.1 |
|  |  |  |  |  | 47.3 | 6.2 |  |  | 9.2 | 12.5 |
|  |  | 160 | 0.4 | 32 | 21.6 | 17.1 | 11.2 | 3.8 | 5.5 | 6.0 |
|  |  |  |  |  | 21.1 | 19.4 | 10.6 | 3.4 | 6.0 | 5.1 |
|  |  | 180 | 0.4 | 34 | 1.8 | 28.0 | 18.7 | 7.5 |  |  |
|  |  |  |  |  | 1.8 | 27.7 | 18.6 | 7. |  |  |

TABLE II

HPA AMINATION

| Ex. | CATALYST | TEMP. (°C.) | LHSV | SAMPLE (g) | CONC. (%) APO | CONC. (%) 1,3-DAP | CONC. (%) DPTA | CONC. (%) TPTA | CONC. (%) PDO |
|---|---|---|---|---|---|---|---|---|---|
| Ex. 3 | Ni-1404, T 3/16" 69% Ni/NiO, Engelhard | 100 | 0.4 | 29 | 76.5 | 2.2 |  |  | 2.9 |
|  |  |  |  |  | 79.5 | 2.2 |  |  | 2.6 |
|  |  | 120 | 0.4 | 30 | 80.6 | 1.6 |  |  | 2. |
|  |  |  |  |  | 83.8 |  |  |  | 2.5 |
|  |  |  |  |  | 82.7 | 1.2 |  |  | 2.4 |
|  |  | 140 | 0.4 | 31 | 74.4 | 3.6 |  |  | 2.6 |
|  |  |  |  |  | 74.9 | 3.7 |  |  | 2.8 |
|  |  | 160 | 0.4 | 31 | 53.5 | 9.5 |  |  | 3.2 |
|  |  |  |  |  | 55.2 | 9.5 |  |  | 3.5 |
|  |  | 180 | 0.4 | 27 | 40.7 | 11.4 |  |  | 3.6 |
|  |  |  |  |  | 40.8 | 12.4 | 1.1 |  | 3.6 |
|  |  |  |  |  | 40.4 | 12.1 | 1.1 |  | 3.8 |
|  |  | 200 | 0.4 | 31 | 8.2 | 13.6 | 1.0 |  | 4.0 |
|  |  |  |  |  | 8.0 | 13.2 | 1.2 |  | 3.8 |

TABLE III

HPA AMINATION

| Ex. | CATALYST | TEMP. (°C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 4 | Raney Co., Grace 54% Co + Ni, R-2786 | 100 | 1.0 | 44 | 31.6 |  |  |  | 14.2 | 31.9 |
|  |  |  |  |  | 33.3 |  |  |  | 14.5 | 31.1 |
|  |  | 120 | 1.0 | 38 | 35.5 |  |  |  | 13.3 | 31.7 |
|  |  |  |  |  | 35.9 |  |  |  | 13.3 | 30.3 |
|  |  | 140 | 1.0 | 48 | 33.3 | 1.9 |  |  | 11.8 | 24.2 |
|  |  |  |  |  | 34.4 | 1.8 |  |  | 12.4 | 22.1 |
|  |  | 160 | 1.0 | 46 | 10.2 | 16.6 | 6.9 | 1.5 | 1.6 |  |
|  |  |  |  |  | 10.2 | 17.5 | 6.8 | 1.3 | 1.8 |  |

TABLE III-continued

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| | | 180 | 1.0 | 34 | 4.3 | 18.1 | 6.8 | 2.0 | | |
| | | | | | 4.4 | 18.7 | 7.0 | 1.6 | | |
| | | 200 | 1.0 | 47 | 5.2 | | | | | |
| | | | | | | 4.4 | | | | |

TABLE IV

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 5 | Raney Ni, Grace 55% Ni+ Mo, R-3142 | 100 | 0.4 | 35 | 62.5 | | | | 5.8 | 8.0 |
| | | | | | 63.2 | | | | 5.5 | 7.1 |
| | | 120 | 0.4 | 30 | 71.9 | 2.5 | | | 3.4 | 7.1 |
| | | | | | 71.8 | 2.6 | | | 3.5 | 3.9 |
| | | 140 | 0.4 | 33 | 61.3 | 9.3 | 1.2 | | 3.3 | 1.8 |
| | | | | | 71.6 | 6.3 | | | 2.8 | 1.0 |
| | | 160 | 0.4 | 32 | 29.8 | 2.7 | 5.1 | | 2.8 | |
| | | | | | 37.0 | 20.8 | 3.4 | | 2.9 | |
| | | 180 | 0.4 | 22 | 19.9 | 22.4 | 8.1 | 2.0 | 1.6 | |
| | | | | | 19.9 | 21.8 | 8.0 | 2.0 | 1.7 | |
| | | 200 | 0.4 | 33 | 4.8 | 8.7 | | | 1.7 | |
| | | | | | 5.0 | 10.3 | 1.0 | | 1.5 | |

TABLE V

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 6 | Raney Ni, Grace 47% Ni, R-5886 | 100 | 0.4 | 37 | 61.1 | | | | 3.7 | 7.3 |
| | | | | | 58.1 | | | | 4.4 | 7.2 |
| | | 120 | 0.4 | 35 | 75.0 | | | | 2.0 | 3.4 |
| | | | | | 74.7 | | | | 2.2 | 3.3 |
| | | 140 | 0.4 | 39 | 46.1 | 13.0 | 1.1 | | 4.5 | 1.7 |
| | | | | | 46.2 | 10.0 | 0.9 | | 3.1 | 1.4 |
| | | 160 | 0.4 | 34$^a$ | 3.0 | 25.7 | 1.8 | | 3.6 | 1.8 |
| | | | | | | 28.1 | | | | |
| | | 180 | 0.4 | 40$^b$T | $^b$ | | | | | |
| | | | | B | 34.1 | 25.5 | 4.0 | | 2.9 | 2.7 |
| | | | | | 34.3 | 25.7 | 3.8 | | 2.5 | 2.6 |

$^A$Dark red liquid product
$^b$Two-phase liquid product, lighter phase is hydrocarbon only

TABLE VI

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 7 | Ni-3275, E 1/16", 50% Ni Engelhard | 100 | 0.4 | 79.8 | 14.0 | | | | 1.1 | |
| | | | | | 24.8 | | | | 0.7 | |
| | | 120 | 0.4 | 26.6 | 75.6 | 4.0 | 0.7 | | 2.2 | 0.9 |
| | | | | | 74.2 | 1.1 | 0.7 | | 2.1 | 0.9 |
| | | 140 | 0.4 | 17.9 | 73.2 | 6.8 | 1.0 | | 2.1 | 1.2 |
| | | | | | 71.2 | 6.0 | 1.1 | | 2.1 | 1.3 |

TABLE VI-continued

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| | | 160 | 0.4 | 20.8 | 54.1 | 16.8 | 2.9 | 0.4 | | 2.1 |
| | | | | | 59.7 | 16.7 | 1.7 | | 2.1 | 0.6 |
| | | 180 | 0.4 | 29.9 | 24.5 | 32.4 | 10.1 | 1.7 | 1.8 | 3.5 |
| | | | | | 22.0 | 30.4 | 8.5 | 1.7 | 1.6 | 2.9 |

TABLE VII

3-AMINO-1-PROPANOL AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 8 | Raney Co., Grace[a], 52% Co + Ni/Mo R-2796 | 180 | 0.9 | 1[a] | 39 | 14.8 | 29.1 | 17.7 | 8.4 | 2.6 |
| | | | | | | 13.8 | 27.6 | 19.4 | 7.8 | 3.0 |
| | | 180 | 0.4 | 1 | 4 | 7.0 | 33.7 | 22.8 | 10.6 | 1.7 |
| | | 180 | 0.4 | 2 | 42 | 4.5 | 30.8 | 22.6 | 11.7 | 0.7 |
| | | 180 | 0.4 | 3 | 43 | 4.6 | 28.7 | 21.5 | 11.8 | 0.6 |
| | | 180 | 0.4 | 4[b] | 25 | 14.3 | 26.0 | 21.7 | 12.5 | 1.0 |
| | | 185 | 0.4 | 5 | 36 | 6.4 | 25.1 | 21.2 | 12.0 | 0.8 |
| | | | 0.4 | | | 7.8 | 26.5 | 20.7 | 12.5 | 0.8 |
| | | 185 | 0.4 | 6 | 31 | 4.2 | 26.4 | 18.8 | 11.9 | 0.4 |

[a]Catalyst charge: 28 cc, run each day, unit shut down overnight
[b]Unit shut down over 3 days

TABLE VIII

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 9 | Ni-3250, T3/16" Engelhard, 58% Ni/NiO | 100 | 0.4 | 17.8 | 78.0 | 7.1 | 1.8 | 1.0 | 0.7 | 1.8 |
| | | | | | 78.6 | 7.1 | 1.6 | 0.8 | 0.8 | 1.6 |
| | | 120 | 0.4 | 34.1 | 54.5 | 8.8 | 4.3 | 0.2 | 2.8 | 4.8 |
| | | | | | 54.7 | 8.9 | 4.1 | 0.2 | 2.7 | 5.1 |
| | | 140 | 0.4 | 35.9[a] | 41.4 | 2.4 | 1.4 | 0.3 | 3.6 | 2.1 |
| | | 160 | 0.4 | 15.3[b] | 54.3 | 8.2 | 3.4 | 0.2 | 2.5 | 5.8 |
| | | | | | 50.7 | 6.9 | 2.8 | 0.2 | 2.9 | 5.7 |
| | | 180 | 0.4 | 26.9 | 54.8 | 4.4 | 3.6 | 0.1 | 2.5 | 5.6 |
| | | | | | 56.9 | 4.1 | 4.0 | 0.2 | 2.7 | 6.2 |
| Ex. 10 | C46-7-03, E 1/16" United, 50-65% Ni/NiO | 100 | 0.4 | 64.6 | 75.4 | 1.0 | 0.5 | 0.1 | 2.5 | 2.0 |
| | | | | | 78.3 | 1.0 | 0.5 | | 2.6 | 2.3 |
| | | 120 | 0.4 | 36.1 | 75.7 | 1.2 | 0.4 | 0.1 | 2.5 | 2.2 |
| | | | | | 76.2 | 1.2 | 0.4 | 0.1 | 2.5 | 2.2 |
| | | 140 | 0.4 | 29.0 | 72.3 | 2.4 | 0.6 | 0.2 | 2.6 | 2.1 |
| | | | | | 72.4 | 2.4 | 0.5 | 0.1 | 2.6 | 2.1 |
| | | 160 | 0.4 | 17.8 | 71.9 | 2.6 | 0.8 | 0.1 | 2.7 | 1.8 |
| | | | | | 71.6 | 2.5 | 0.7 | 0.1 | 2.7 | 2.2 |
| | | 180 | 0.4 | 49.6 | 56.7 | 10.3 | 3.1 | 0.2 | 2.8 | 4.2 |
| | | | | | 58.1 | 9.9 | 3.2 | 0.2 | 2.9 | 4.7 |

[a]Reactor temperature controller malfunctioned, one zone exceeds 200° C.
[b]Reactor recatalyzed with fresh Ni-3250.

Example 11

Comparison Example

Example 11 was carried out in exactly the same manner as Examples 1 through 10 except the catalyst used was a cobalt-copper catalyst which is known in the art. The data in Table IX clearly shows that catalyst is much less effective in the one-step amination. For example, in Table VI, using Raney cobalt, at 180° C., the percent of the effluent sample which comprised 1,3-diaminopropane was 32.4% and 30.4%, while using the cobalt copper catalyst the amount was 7.8%.

TABLE IX (Comparison Data)

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO | CONC. (%) (HOC$_3$)$_2$NH |
|---|---|---|---|---|---|---|---|---|---|---|
| Ex. 11 | L6540-6-1 1/32" E Engelhard[a] | 100 | 0.4 | 77[c] | 54.6 | 8.1 | 0.8 | | 9.9 | 2.9 |
| | | | | | 54.9 | 7.8 | 0.8 | | 10.2 | 2.8 |
| | | 120 | 0.4 | 84[d] | 78.0 | 3.4 | | | 6.1 | 3.9 |
| | | | | | 77.7 | 3.3 | | | 5.5 | 4.2 |
| | | 140 | 0.4 | 91[e] | 75.3 | 3.2 | | | 4.4 | 4.7 |
| | | | | | 75.4 | 3.2 | | | 4.2 | 4.7 |
| | | 160 | 0.4 | 94[e] | 66.4 | 5.1 | | | 4.3 | 4.5 |
| | | | | | 66.4 | 5.1 | | | 4.6 | 4.3 |
| | | 180 | 0.4 | 83[e] | 50.8 | 7.8 | 1.0 | 0.8 | 4.8 | 3.9 |
| | | | | | 50.9 | 7.8 | 1.0 | 0.9 | 4.7 | 4.0 |

[a]A cobalt-copper catalyst
[c]Sample liquid dark green; Cu, 0.04%; Na, 0.04%
[d]Sample liquid yellow; Na, 0.04%; Si, 0.02%
[e]Sample liquid pale yellow; Na, 0.02%; Si, 0.03–0.04%

Examples 12 and 13

Examples 12 and 13 represent the two-step embodiment of the process. Data for Step (1) is shown in Table X and data for Step 2 is shown in Table XI. In Step (1), using a supported nickel catalyst, the intermediate 3-amino-propanol is obtained in ca. 80% yield at 120° C. In Step 2, using a Raney cobalt catalyst with Mo and Ni promoters, 1,3-diaminopropane is generated in ca. 50% yields at quantitative 3-amino-1-propanol conversion levels. In this case the amination temperature is 180° C.

TABLE X

HPA AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) PDO |
|---|---|---|---|---|---|---|---|---|---|
| Ex. 12 | Ni-1404, T 3/16" 68% Ni Engelhard | 100 | 0.4 | 29 | 76.5 | 2.2 | | | 2.9 |
| | | | | | 79.5 | 2.2 | | | 2.6 |
| | | 120 | 0.4 | 30 | 80.6 | 1.6 | | | 2.5 |
| | | | | | 83.8 | | | | 2.5 |
| | | | | | 82.7 | 1.2 | | | 2.4 |
| | | 140 | 0.4 | 31 | 74.4 | 3.6 | | | 2.6 |
| | | | | | 74.9 | 3.7 | | | 2.8 |
| | | 160 | 0.4 | 31 | 53.5 | 9.5 | | | 3.2 |
| | | | | | 55.2 | 9.5 | | | 3.5 |
| | | 180 | 0.4 | 27 | 40.7 | 11.4 | | | 3.6 |
| | | | | | 40.8 | 12.4 | 1.1 | | 3.6 |
| | | | | | 40.4 | 12.1 | 1.1 | | 3.8 |
| | | 200 | 0.4 | 31 | 8.2 | 13.6 | 1.0 | | 4.0 |
| | | | | | 2.0 | 13.2 | 1.2 | | 3.8 |

TABLE XI

3-AMINO-1-PROPANOL AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) (HOC$_3$)$_2$NH |
|---|---|---|---|---|---|---|---|---|---|
| Ex. 13 | Raney, Co., Grace, 52% Co + Ni/Mo R-2796 | 160 | 0.4 | 31[a] | 14.9 | 30.2 | 23.0 | 14.1 | 10.0 |
| | | | | | 18.7 | 39.7 | 27.0 | | 12.5 |
| | | 180 | 0.4 | 31 | 7.1 | 42.6 | 26.4 | | |
| | | | | | 7.5 | 42.5 | 31.9 | | |
| | | 200 | 0.4 | 31 | | 3.2 | | | |
| | | | | | | 3.8 | | | |

TABLE XI-continued

3-AMINO-1-PROPANOL AMINATION

| Ex. | CATALYST | TEMP. (° C.) | LHSV | SAMPLE (g) | CONC. (%) APO | CONC. (%) 1,3-DAP | CONC. (%) DPTA | CONC. (%) TPTA | CONC. (%) (HOC$_3$)$_2$NH |
|---|---|---|---|---|---|---|---|---|---|
|  |  | 180 | 0.4 | 96 |  | 47.0 | 25.4 |  |  |
|  |  |  |  |  |  | 49.4 | 28.7 |  |  |
|  |  |  |  |  | 1.3 | 35.0 | 24.8 | 11.6 |  |
|  | Distillation | Cut #3 |  |  |  | 81.1 |  |  |  |
|  |  | Cut #4 |  |  | 0.7 | 87.7 |  |  |  |
|  |  | Cut #5 |  |  |  | 28.7 | 9.6 |  |  |

Example 14

In this example, a 20 gm solution of 3-hydroxypropanal in methyl tert-butyl ether was hydroaminated with ammonia and hydrogen in a 100 cc batch autoclave in the presence of 3 gm of Raney cobalt catalyst (52% cobalt plus nickel/molybdenum promoters, R-2796). Operating conditions were 180° C., 2300 psi pressure, hydroamination was continued for 4 hours. The product liquid, after workup, was found to contain 1,3-diaminopropane.

We claim:

1. A process for the production of diaminoalkanes which comprises:
   introducing into a reactor one or more by hydroxyalkanals; reacting said hydroxyalkanal in the presence of excess ammonia and hydrogen and in the presence of a catalyst comprising at least one metal selected from nickel or cobalt, or a mixture thereof, optionally on a support or as a bulk-metal catalyst; reacting said hydroxyalkanal at a temperature of from 140° C. to 180° C. at a pressure of at least 500 psi; and separating the diaminoalkane product.

2. The process of claim 1 wherein the hydroxyalkanal is 3-hydroxypropanal and the product dialkylamine is 1,3-diaminopropane.

3. The process of claim 2 wherein the pressure is from 500 psi to 5000 psi.

4. The process of claim 3 wherein the pressure is from 1000 psi to 3000 psi.

5. The process of claim 2 further comprising introducing the 3-hydroxypropanal into the reactor in a solvent selected from the group consisting of methyl tertiary-butyl ether, tertiary-butanol, and water.

6. The process of claim 5 wherein the solvent is water.

7. The process of claim 2 wherein the molar ratio of ammonia to hydroxyalkanal is 5 to 200:1.

8. The process of claim 2 wherein the hydrogen is fed to the reactor at a rate of 0.1–100 mole hydrogen/mole 3-hydroxypropanal.

9. The process of claim 1 wherein the catalyst contains on an oxide-free basis about 10–80% cobalt.

10. The process of claim 9 wherein the catalyst further comprises from about 10 to 80% cobalt, plus a nickel and molybdenum promoter.

11. The process of claim 1 wherein the catalyst comprises on an oxide-free basis from about 10 to 80 wt % nickel, plus a molybdenum promoter.

12. The process of claim 9 further comprising the use of one or more promoters selected from the group consisting of Group IB and Group VIB of the Periodic Table.

13. The process of claim 12 wherein the promoters are selected from the group consisting of tungsten, copper, molybdenum, and chromium.

14. The process of claim 9 wherein the catalyst comprises on an oxide-free basis from about 50 to 60% cobalt.

15. The process of claim 1 wherein the catalyst comprises at least one metal selected from the group consisting of nickel and cobalt on a support.

16. The process of claim 15 wherein the support is selected from Groups IIa, IIIa, IVa, or Va of the Periodic Table.

17. The process of claim 15 wherein the support is selected from the group consisting of magnesia, alumina, silica, zirconia, and titania, as well as mixtures thereof.

18. A two-step process for the production of 1,3-diaminopropane which comprises:
   a) introducing into a reactor 3-hydroxypropanal, reacting said 3-hydroxypropanal in the presence of excess ammonia and hydrogen and in the presence of a nickel catalyst at a temperature of at least 50° C. and a pressure of at least 500 psi; generating an intermediate comprising 3-amino-1-propanol,
   b) reacting said 3-amino-1-propanol in the presence of excess ammonia and hydrogen and in the presence of a cobalt catalyst, at a temperature of 140 to 200° C. and a pressure of 1000 to 3000 psi; and isolating said 1,3-diaminopropane.

19. The process of claim 18 wherein the temperature in the first step is 100–150° C.

20. The process of claim 18 wherein the pressure in step a) is from 500 psi to 5000 psi.

21. The process of claim 18 further comprising introducing the 3-hydroxypropanal into the reactor in a solvent comprising water.

22. The process of claim 18 wherein the molar ratio of ammonia to 3-hydroxypropanal is 5–200:1.

23. The process of claim 18 wherein the hydrogen is fed to the reactor at a rate of 0.1–100 mole hydrogen/mole 3-hydroxypropanal.

24. The process of claim 1 wherein the nickel catalyst is a bulk-metal nickel catalyst.

25. The process of claim 24 wherein the nickel catalyst contains about 10–80% nickel.

26. The process of claim 24 wherein the bulk-metal nickel catalyst also contains molybdenum oxide.

27. The process of claim 24 wherein the bulk-metal nickel catalyst also contains copper and chromium.

* * * * *